United States Patent
Griffiths et al.

(10) Patent No.: US 9,642,629 B2
(45) Date of Patent: May 9, 2017

(54) SYSTEM AND METHOD FOR FORMING A CURVED TUNNEL IN BONE

(71) Applicant: Specialty Surgical Instrumentation Inc., Antioch, TN (US)

(72) Inventors: Jerry R. Griffiths, Norwell, MA (US); Jose Fernandez, Wrentham, MA (US)

(73) Assignee: Specialty Surgical Instrumentation Inc., Antioch, TN (US)

( * ) Notice: Subject to any disclaimer, the term of this patent is extended or adjusted under 35 U.S.C. 154(b) by 614 days.

(21) Appl. No.: 14/084,460

(22) Filed: Nov. 19, 2013

(65) Prior Publication Data
US 2014/0171948 A1   Jun. 19, 2014

Related U.S. Application Data

(60) Provisional application No. 61/728,479, filed on Nov. 20, 2012.

(51) Int. Cl.
| A61B 17/00 | (2006.01) |
| A61B 17/16 | (2006.01) |
| A61B 17/17 | (2006.01) |
| A61B 17/04 | (2006.01) |

(52) U.S. Cl.
CPC ...... *A61B 17/1637* (2013.01); *A61B 17/1642* (2013.01); *A61B 17/1796* (2013.01); *A61B 17/04* (2013.01); *A61B 17/1631* (2013.01); *A61B 17/1633* (2013.01); *A61B 2017/00309* (2013.01); *A61B 2017/00323* (2013.01); *Y10T 29/49826* (2015.01)

(58) Field of Classification Search
None
See application file for complete search history.

(56) References Cited

U.S. PATENT DOCUMENTS

| 7,081,119 | B2 | 7/2006 | Stihl |
| 2009/0287219 | A1 | 11/2009 | Hart |
| 2009/0326538 | A1* | 12/2009 | Sennett .............. A61B 17/1642 606/80 |
| 2010/0191248 | A1 | 7/2010 | Mehta et al. |
| 2012/0245586 | A1 | 9/2012 | Lehenkari et al. |

FOREIGN PATENT DOCUMENTS

WO    WO2008099176 A1    8/2008

OTHER PUBLICATIONS

International Search Report, ISA/KR, Feb. 26, 2014.

* cited by examiner

*Primary Examiner* — Sameh Boles
(74) *Attorney, Agent, or Firm* — Hayes Soloway PC (57) ABSTRACT

A drill system for forming a curved tunnel in a bone includes a drill bit guidance device. The drill bit guidance device includes an elongated stationary outer tube extending along a first axis and an elongated inner tube. The elongated inner tube is configured to slidably move within the elongated stationary outer tube along the first axis and to exit from a distal end of the elongated outer tube. The elongated inner tube has a partially slotted distal end portion including a plurality of semi-cross-sectional slots extending perpendicular to the first axis. Each slot is configured to collapse inward in the slot direction when exiting the distal end of the elongated outer tube, thereby curving the distal end portion of the elongated inner tube.

21 Claims, 13 Drawing Sheets

SYSTEM AND METHOD FOR FORMING A CURVED TUNNEL IN BONE

CROSS REFERENCE TO RELATED CO-PENDING APPLICATIONS

This application claims the benefit of U.S. provisional application Ser. No. 61/728,479 filed on Nov. 20, 2012 and entitled SYSTEM AND METHOD FOR FORMING A CURVED TUNNEL IN BONE, which is commonly assigned and the contents of which are expressly incorporated herein by reference.

FIELD OF THE INVENTION

The present invention relates to a system and a method for forming a curved tunnel in a bone and in particular to device that uses a tube with a slotted front end to form a U-shaped tunnel in the bone.

BACKGROUND OF THE INVENTION

In several surgical procedures opening of curved tunnels in bone is needed. Examples of these type of surgical procedures include rotator cuff repair and Achilles tendon repair where re-attaching of muscle and ligaments to bone is performed.

Prior art technologies for performing these type of surgical procedures involve drilling two separate openings that have intersecting screw paths in order to form the attachment point. These prior art procedures are invasive because they require drilling two separate intersecting openings from two different directions. There is also the possibility that the two drilled openings do not intersect, due to miscalculations of the drill path or inaccuracy in the drilling process. This may result in drilling additional openings in the bone, which increases the level of complexity of the procedure, increases the operation time and also increases the bleeding risk of the patient.

Accordingly, systems and methods that simplify the above mentioned surgical procedures are desirable.

SUMMARY OF THE INVENTION

The present invention provides a system and a method for forming a curved tunnel in a bone by using a drill bit guidance device. The drill bit guidance device includes a tube with a slotted front end, whereby the slots collapse and cause the tube to curve at a predetermined radius as the drill bit moves forward.

The present invention also provides a system and a method for attaching a ligament to a bone by forming a curved tunnel in a bone. The method includes first providing a drill and a drill bit guidance device that guides the drill bit to form a U-shaped curved tunnel. Next, drilling a U-shaped tunnel into a bone by entering into a first bone location with the guided drill bit and exiting from a second bone location. Next, threading a suture through the opened U-shaped tunnel and through the ligament that needs to be attached to the bone, and then attaching the ligament to the bone with the threaded suture.

In general, in one aspect, the invention features drill system for forming a curved tunnel in a bone including a drill bit guidance device. The drill bit guidance device includes an elongated stationary outer tube extending along a first axis and an elongated inner tube. The elongated inner tube is configured to slidably move within the elongated stationary outer tube along the first axis and to exit from a distal end of the elongated outer tube. The elongated inner tube has a partially slotted distal end portion including a plurality of semi-cross-sectional slots extending perpendicular to the first axis. Each slot is configured to collapse inward in the slot direction when exiting the distal end of the elongated outer tube, thereby curving the distal end portion of the elongated inner tube.

Implementations of this aspect of the invention may include one or more of the following features. The drill bit guidance device further includes a drive shaft, a flexible shaft, a drill bit and a flexible actuator rod. The elongated inner tube surrounds the drive shaft, the flexible shaft, and the flexible actuator rod. The drill bit is attached to a distal end of the flexible shaft and a distal end of the drive shaft is attached to a proximal end of the flexible shaft. The flexible actuator rod is arranged parallel to the drive shaft and a distal end of the flexible actuator is attached to the distal end of the elongated inner tube. The curving of the distal end of the elongated inner tube is configured to curve the flexible shaft and to guide the attached drill bit along a curved path. The radius of the curved path is configured to remain constant by maintaining constant the ratio of the length of the drive shaft to the length of the collapsed slotted distal end portion of the elongated inner tube. The drill bit guidance device further includes a universal grip, a handle block, a thrust assembly, and a linkage assembly. The universal grip is attached to the handle block and the handle block has a first through-opening dimensioned to receive the elongated outer tube. The thrust assembly is pivotally linked to the handle block via the linkage assembly and includes a shank chuck, a tube bushing, a thrust end cap, first and second thrust bushings and an actuator slide. The actuator slide has a first through-opening dimensioned to receive the elongated inner tube and the proximal end of the drive shaft is connected to the shank chuck. The proximal ends of the elongated inner tube, the drive shaft and the flexible actuator rod are linked together via the linkage assembly, and the linkage assembly is configured to maintain constant the ratio of the length of the drive shaft to the length of the collapsed slotted distal end portion of the elongated inner tube. The linkage assembly includes first and second vertical links configured to pivotally link the handle block to the elongated inner tube. The linkage assembly further includes first and second horizontal links configured to pivotally link the actuator slide to first and second vertical links, respectively. The linkage assembly further includes third and fourth horizontal links configured to pivotally link the actuator slide to the thrust end cap. The flexible shaft comprises Nitinol wire or stainless steel wire. Each of said slots is wider at the bottom than at the top. The drill system further includes a drill driver having a front opening configured to receive removable attachments, and the drill bit guidance device is configured to be removably attached to the front opening of the drill driver. The thrust assembly is linked to the handle block via a gear mechanism or a cam mechanism.

In general, in another aspect, the invention features a method for forming a curved tunnel in a bone including providing a drill and a drill bit guidance device comprising an elongated stationary outer tube extending along a first axis and an elongated inner tube. The elongated inner tube is configured to slidably move within the elongated stationary outer tube along the first axis and to exit from a distal end of the elongated outer tube. The elongated inner tube comprises a partially slotted distal end portion comprising a plurality of semi-cross-sectional slots extending perpendicular to the first axis. Each slot is configured to collapse inward in the slot direction when exiting the distal end of the elongated outer tube, thereby curving the distal end portion of the elongated inner tube.

In general, in another aspect, the invention features a method for a method for attaching a ligament to a bone including the following steps. First, providing a drill comprising a drill bit guidance device. The drill bit guidance device guides a drill bit to drill and form a U-shaped tunnel in the bone. Next, drilling a U-shaped tunnel into the bone by entering into a first bone location and exiting through a second bone location. Next, threading a suture through the U-shaped tunnel and through a ligament, and then attaching the ligament to the bone by tying the suture.

Among the advantages of this invention may be one or more of the following. The invention provides a method for attaching a ligament to a bone without the use of screws. This eliminates the need for introducing screws or other foreign objects in the bone, which in turn reduces the risks of infection and rejection of the foreign object. The method opens a single curved path, rather than opening at least two separate paths from two different directions and then trying to orient them so that they intersect each other. This reduces the complexity of the surgical procedure, reduces the operation time and reduces the risk of prolonged bleeding. Furthermore, there no need for a separate device for pulling a suture through the intersecting straight paths.

The details of one or more embodiments of the invention are set forth in the accompanying drawings and description bellow. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1A:
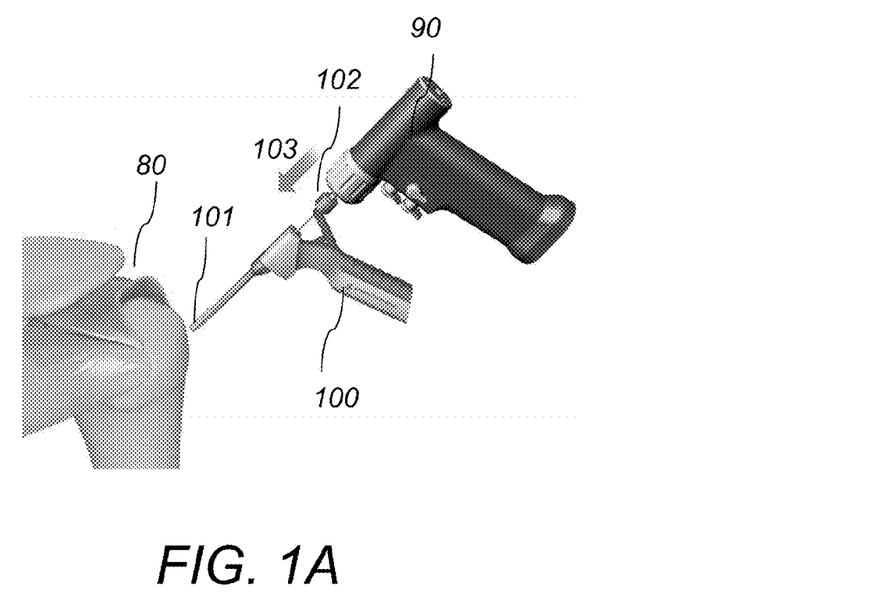
FIG. 1A-FIG. 1E depict schematic views of the steps for performing a ligament re-attachment procedure according to this invention.
Figure 1B:
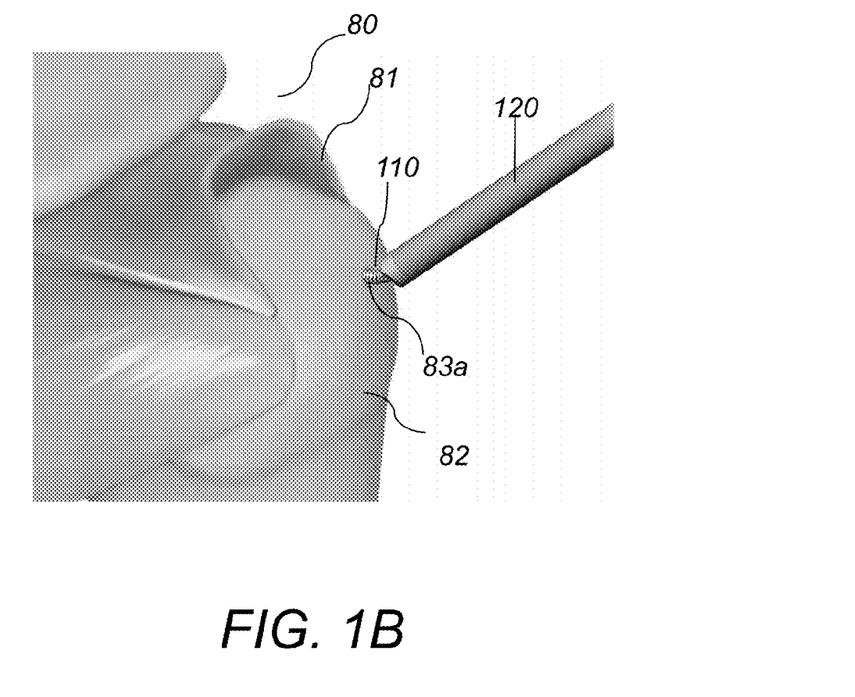
Figure 1C:
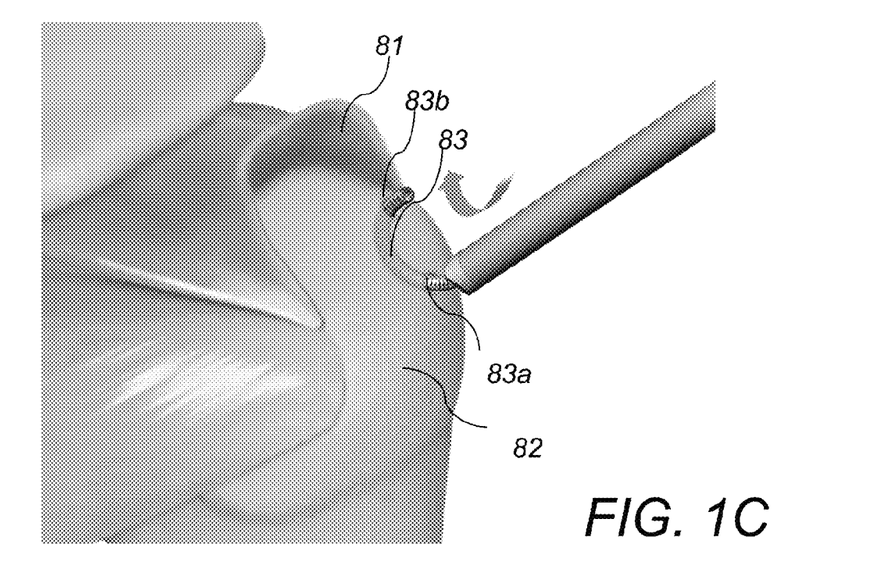
Figure 1D:
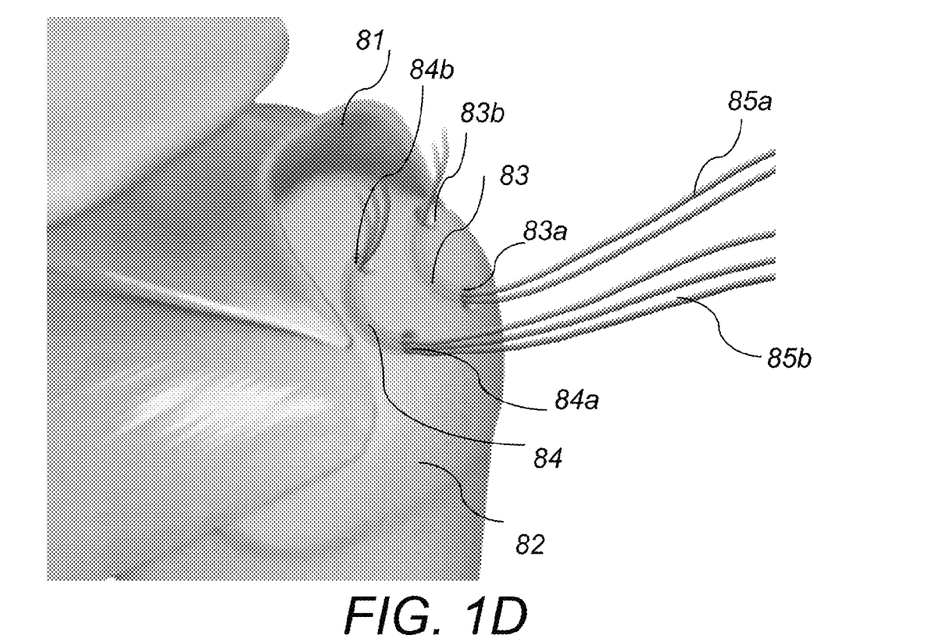
Figure 1E:
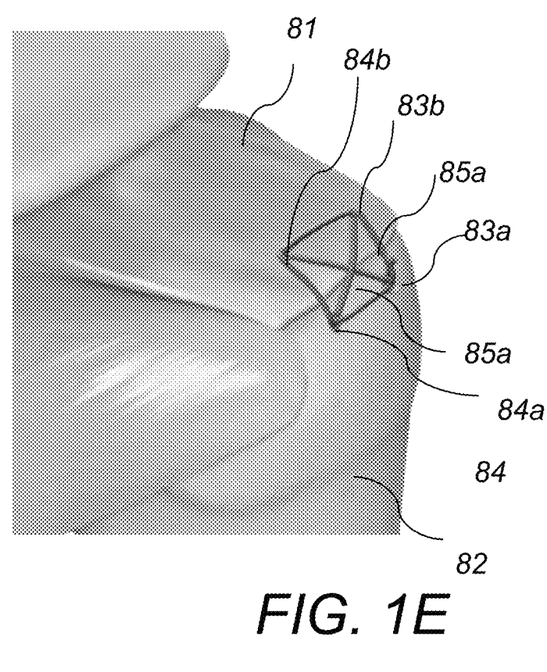

Referring to FIG. 1A-FIG. 1E, a ligament re-attachment surgical procedure in the rotator cuff area 80 includes the following. First, a drill 90 and a drill bit guidance device 100 are provided. Drill bit guidance device 100 is placed in front of drill 90 and includes a mechanism that guides the drill bit to drill a U-shaped curved tunnel. Next, the surgeon creates access to the bone area 82, and holds the distal end 101 of device 100 firmly against the bone 82 with one hand, while the other hand holds the power drill 90 that is attached to the proximal end 102 of the device 100. Next, the surgeon operates the drill 90 so that it rotates and he pushes the drill forward in the direction indicated by arrow 103 toward the distal end 101 of device 100, as shown in FIG. 1A. During this process, a drill bit or burr feeds through the distal end 101 of device 100 and enters a first bone location 83a. As the drill bit feeds out, it is guided by a tube 110 that causes the drill bit to move through a curved path, as shown in FIG. 1C. The curved path has a predetermined radius and forms a U-shaped tunnel 83. The drilling process continues until the drill bit exits the bone from a second bone location 83b. Next, while still holding the device 100 in place, the surgeon retracts the power drill 90 leaving behind an open U-shaped curved tunnel 83. The process is repeated again and a second U-shaped tunnel 84 is opened. Next, sutures 85a, 85c are threaded through the opened U-shaped tunnels 83, 84, respectively, and through the ligament 81 that needs to be attached to the bone 82, as shown in FIG. 1D. Finally, the sutures 85a, 85b are tied and ligament 81 is attached to the bone 82, as shown in FIG. 1E.

Figure 1F:
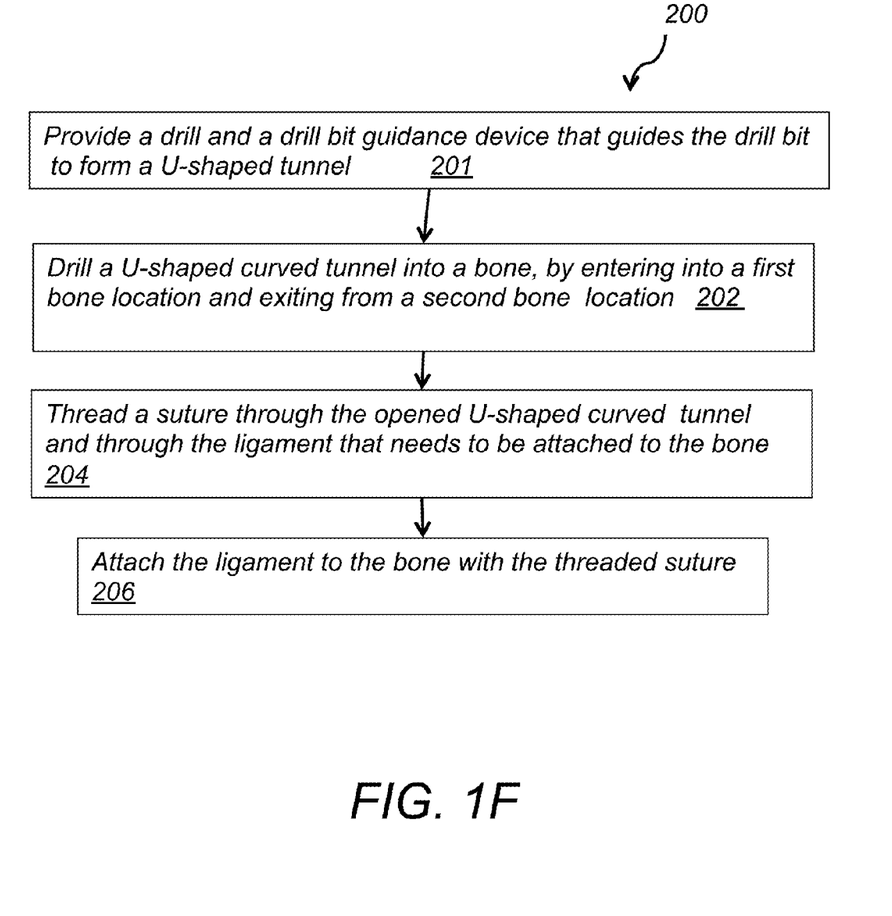
FIG. 1F is a process diagram of a ligament re-attachment procedure according to this invention.

Referring to FIG. 1F, the process diagram 200, for attaching a ligament to a bone includes the following. First, providing a drill and a drill bit guidance device that guides the drill bit to form a U-shaped tunnel (201). Next, drilling a U-shaped tunnel into a bone by entering into a first bone location with the guided drill bit and exiting from a second bone location (202). Next, threading a suture through the opened U-shaped tunnel and through the ligament that needs to be attached to the bone, and then attaching the ligament to the bone with the threaded suture (206).

Figure 2A:
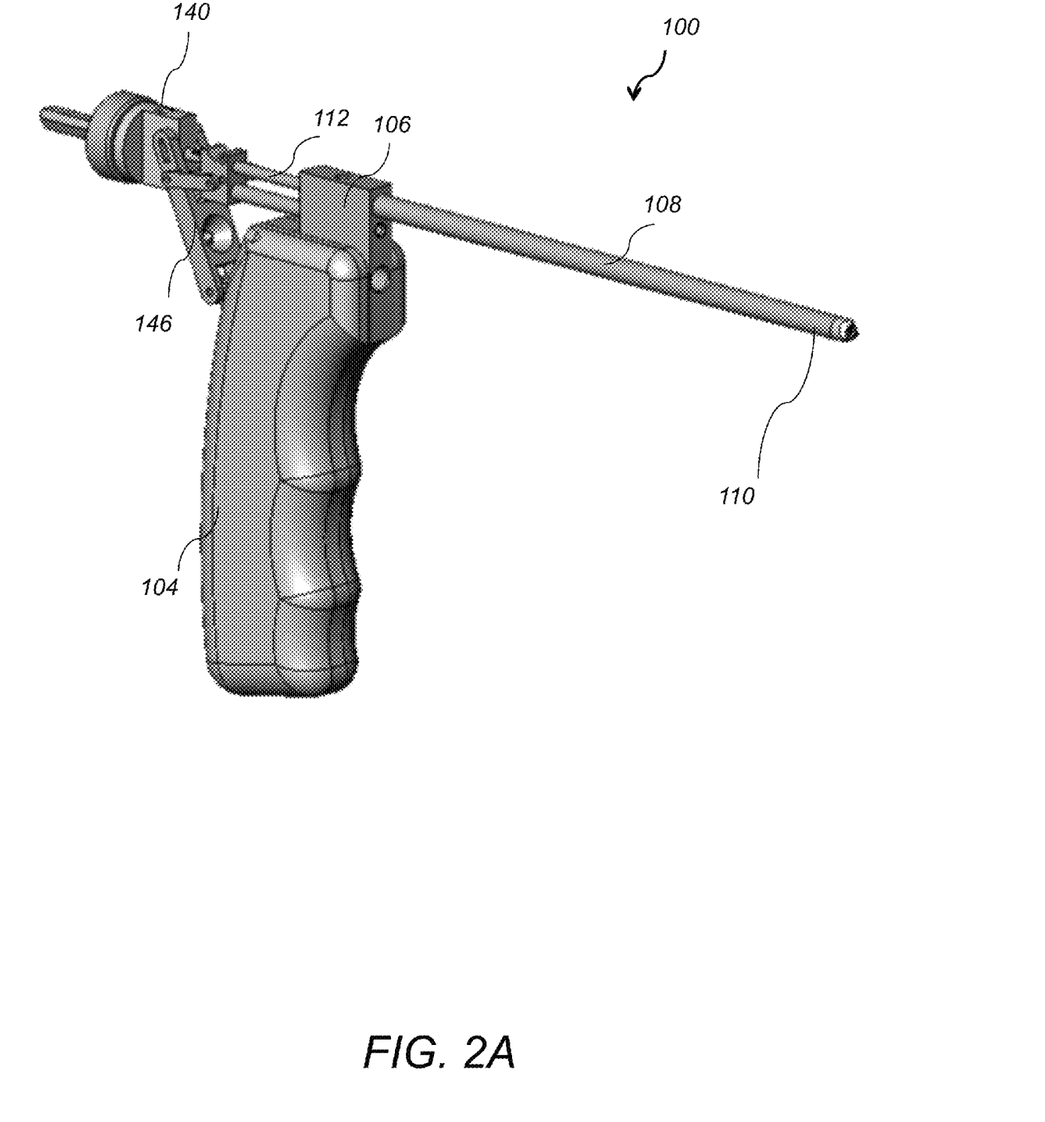
FIG. 2A is a perspective view of a drill bit guidance device according to this invention.

Referring to FIG. 2A, a drill bit guidance device 100 includes a handle 106, a universal grip 104, an outer stationary tube 108, an inner tube assembly 112 and a thrust assembly 140. Thrust assembly 140 transfers the power drill drive motion to a drive shaft 114 that is housed within the inner tube assembly 112, as shown in FIG. 4. The universal grip 104 is attached to handle 106 and is used to hold the device with one hand while holding the power drill 90 with the other hand. Inner rod assembly 112 is housed within the outer stationary tube 108. Handle 106 has a first through opening dimensioned to receive and hold the outer stationary tube 108. Handle 106 also has a second through opening dimensioned to receive and hold a guide rod 148, shown in FIG. 3. Thrust assembly 140 is pivotally linked to handle 106 with link assembly 146.

Figure 3:
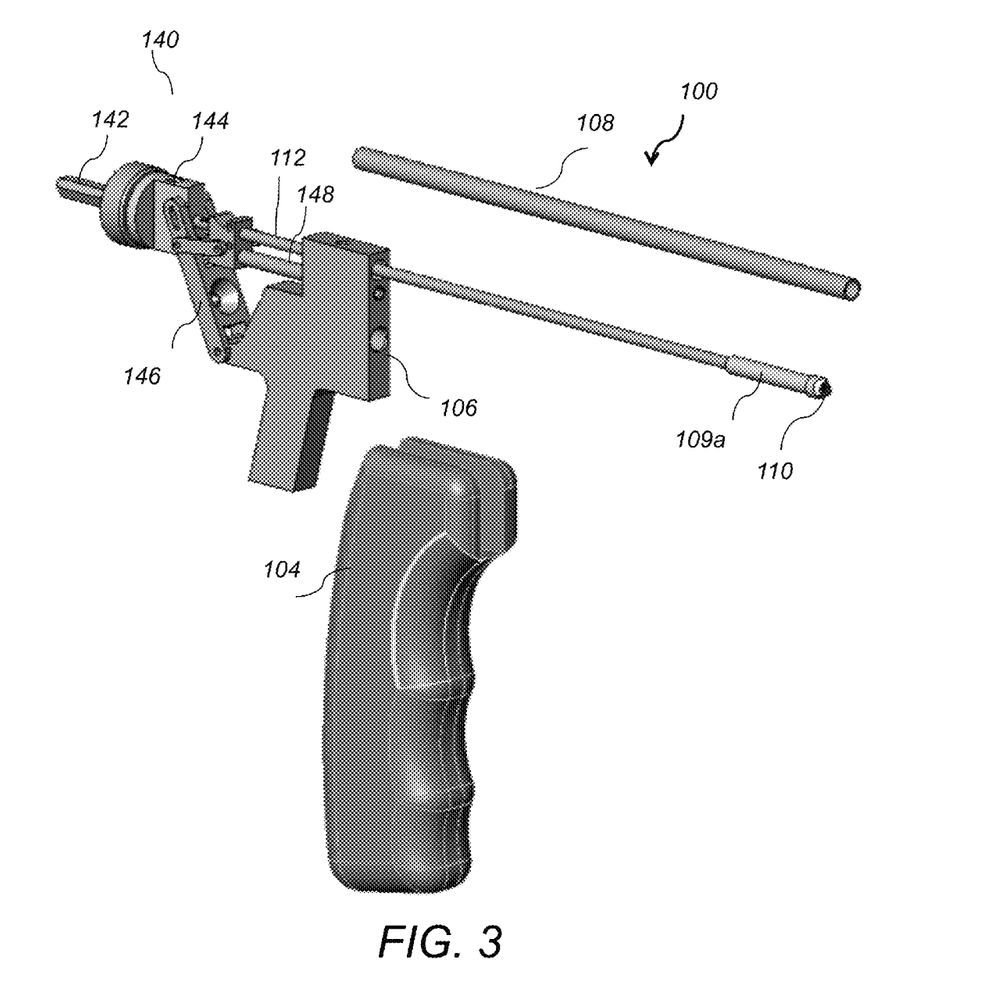
FIG. 3 is a partially exploded view of the drill bit guidance device of FIG. 2A.
Figure 4:
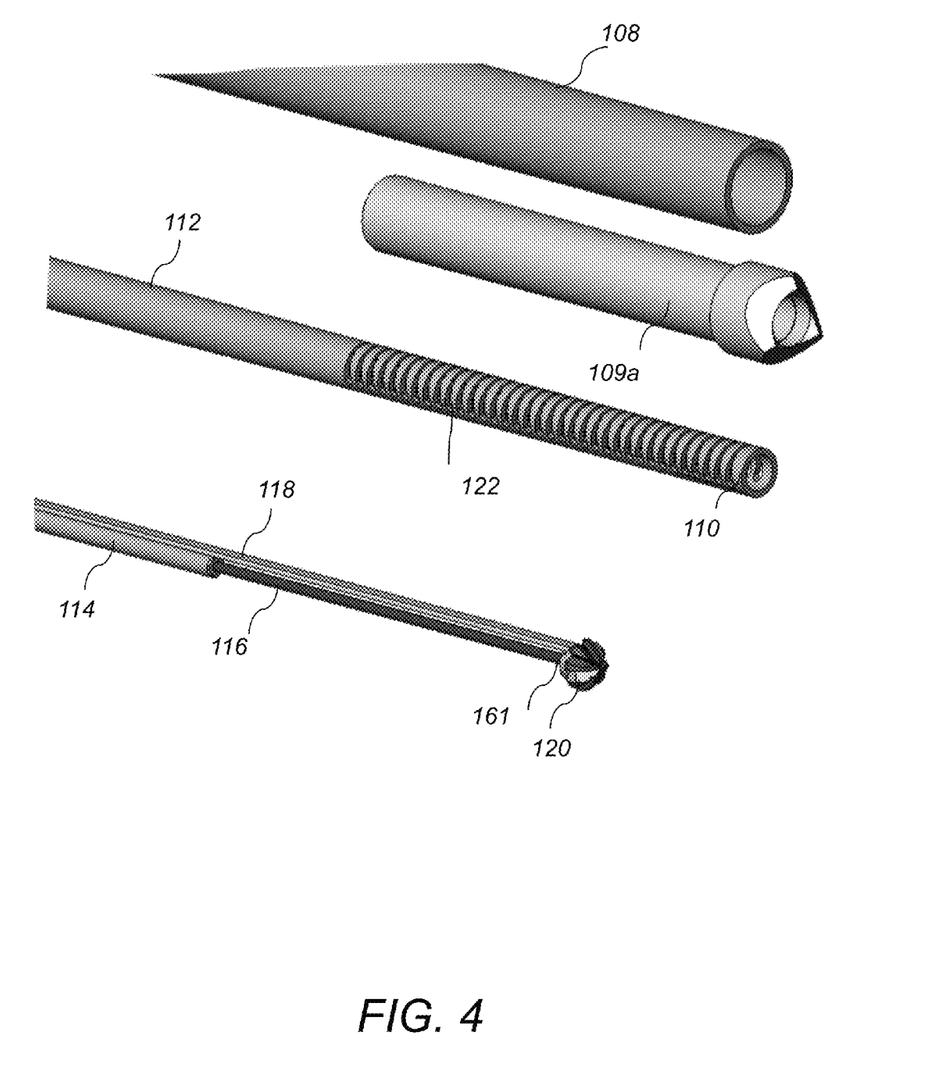
FIG. 4 is an exploded view of the distal end of the drill bit guidance device of FIG. 2A.
Figure 5A:
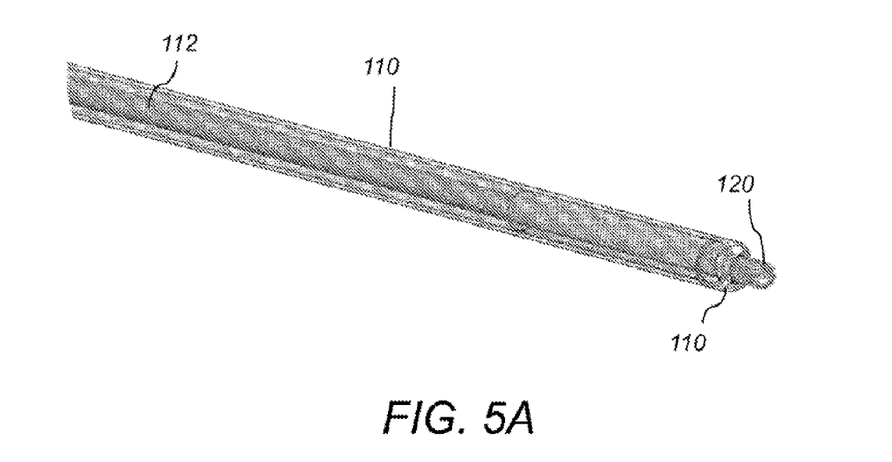
FIG. 5A is a transparent view of the distal end of the drill bit guidance device of FIG. 2A.
Figure 5B:
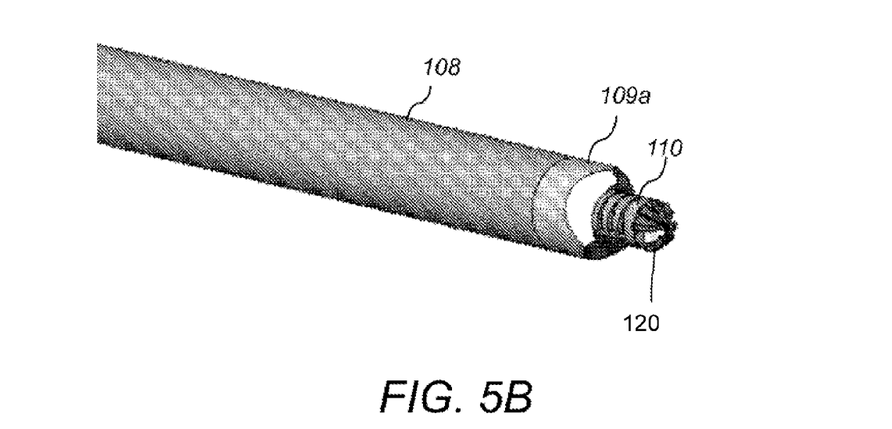
FIG. 5B depicts the distal end of the drill bit guidance device of FIG. 2A with the slotted tube in the "straight" position.
Figure 5C:
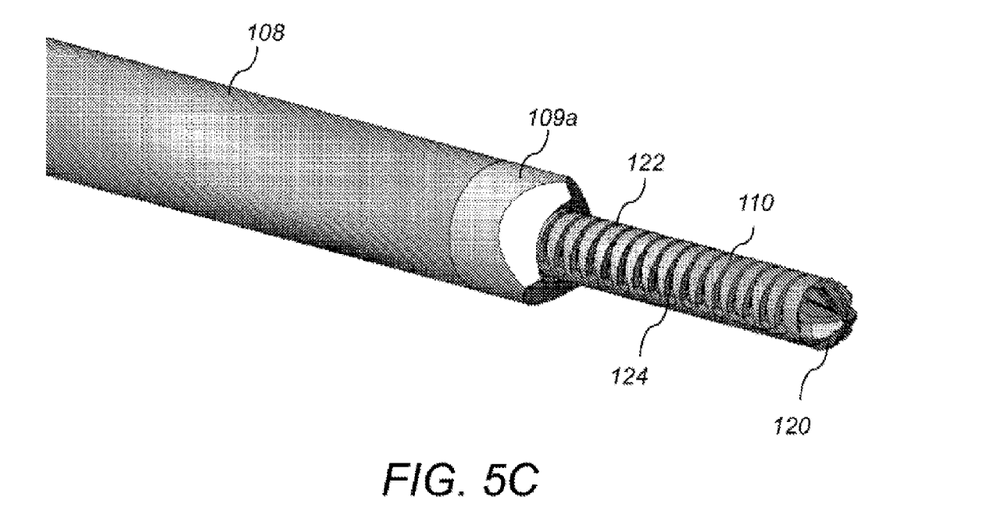
FIG. 5C depicts the distal end of the drill bit guidance device of FIG. 2A with the slotted tube in the "straight" position.
Figure 8A:
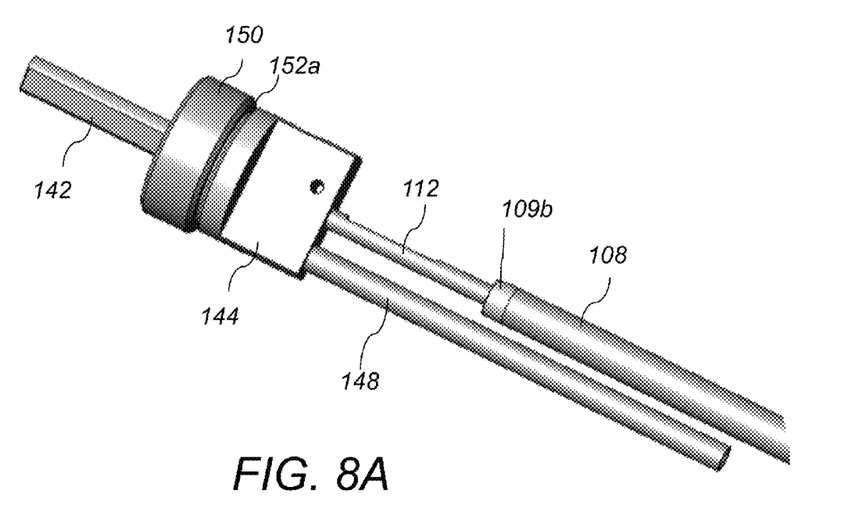
FIG. 8A depicts components of the proximal end of the drill bit guidance device of FIG. 2A.
Figure 8B:
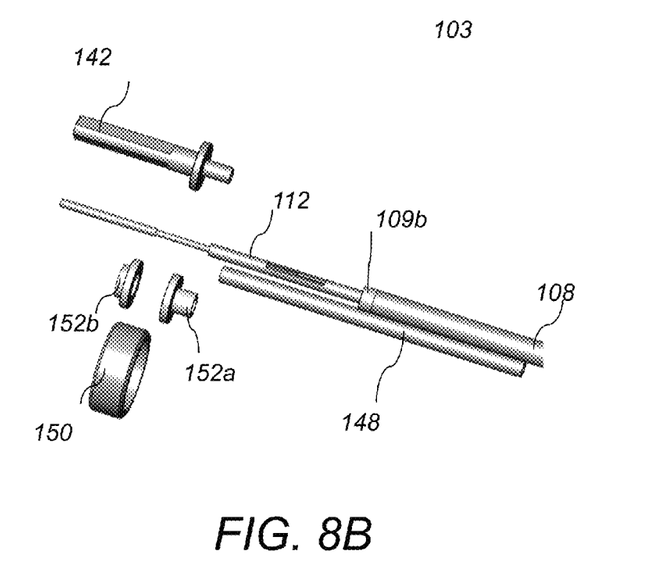
FIG. 8B depicts exploded components of the proximal end of the drill bit guidance device of FIG. 2A.

Referring to FIG. 3 and FIG. 4, inner tube assembly 112 includes a tube 110 with a slotted front portion ("slotted tube"), drive shaft 114, flexible shaft 116, flexible actuator rod 118 and drill bit 120. Drive shaft 114 has a distal end attached to the flexible shaft 116 and flexible shaft 116 is attached to the drill bit 120 with a front end bushing 161. Flexible shaft 116 allows the drill bit 120 to curve and follow the curving of the slotted tube 110, as will be described below. In one example, flexible shaft 116 is made of Nitinol wire, stainless steel wire or cable. Flexible actuator rod 118 is arranged parallel to the drive shaft 114 and has a distal end that is connected to the distal end of the slotted tube 110. The assembled drive shaft 114, flexible shaft 116, drill bit 120, and actuator rod 118 are dimensioned to be housed and move within the slotted tube 110 and slotted tube 110 is dimensioned to be housed and move within the stationary outer tube 108. A front end tube bushing 109*a* supports the distal end of the drive shaft assembly within the front end of the outer tube 108. Similarly, a back end tube bushing 109*b* supports the proximal end of the drive shaft assembly within the back end of the outer tube 108*b*, as shown in FIG. 8A. The slotted front portion of slotted tube 110 includes slots 122 that are slightly wider at the bottom of each slot 124 than at the top of the slot, as shown in FIG. 5C.

Figure 6A:
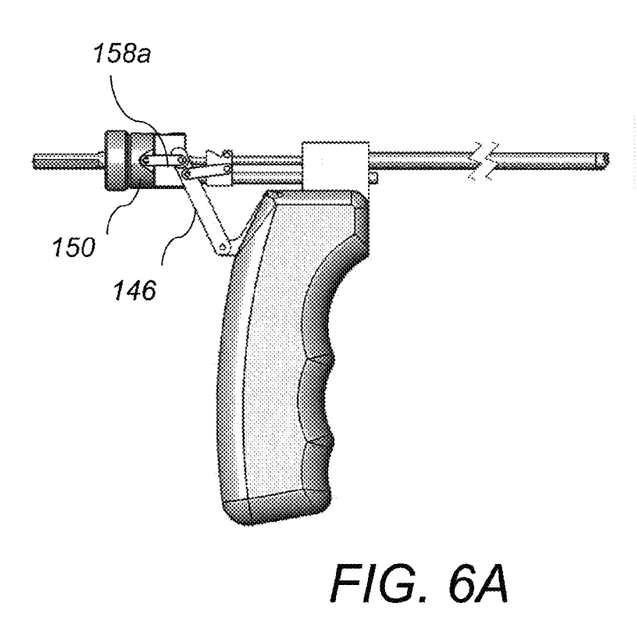
FIG. 6A depicts a side view of another embodiment of the drill bit guidance device with the slotted tube in the "straight" position.
Figure 6B:
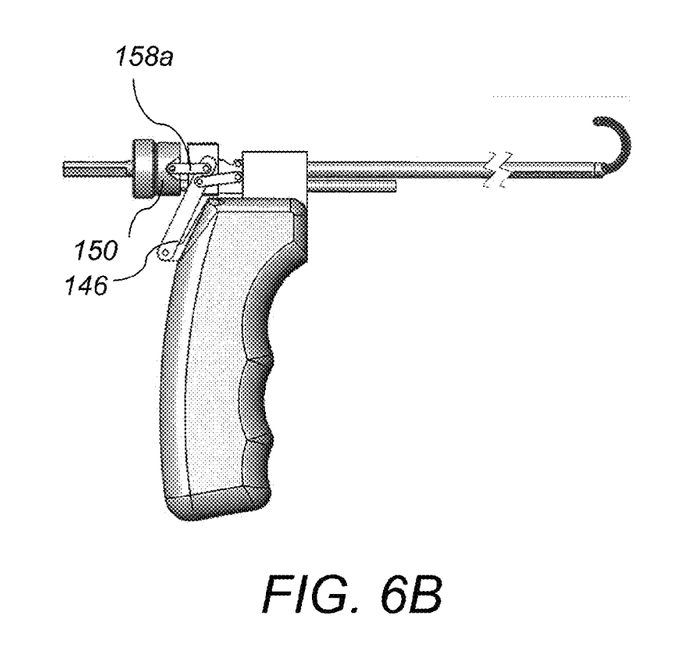
FIG. 6B depicts a side view of the embodiment of FIG. 6A of the drill bit guidance device with the slotted tube in the "curved" position.
Figure 7A:
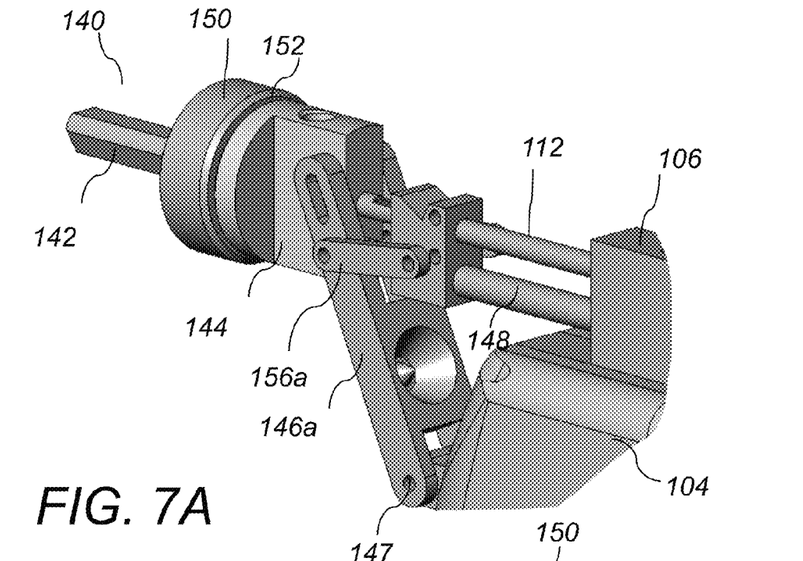
FIG. 7A depicts an enlarged right side view of the thrust assembly of the drill bit guidance device of FIG. 2A.
Figure 7B:
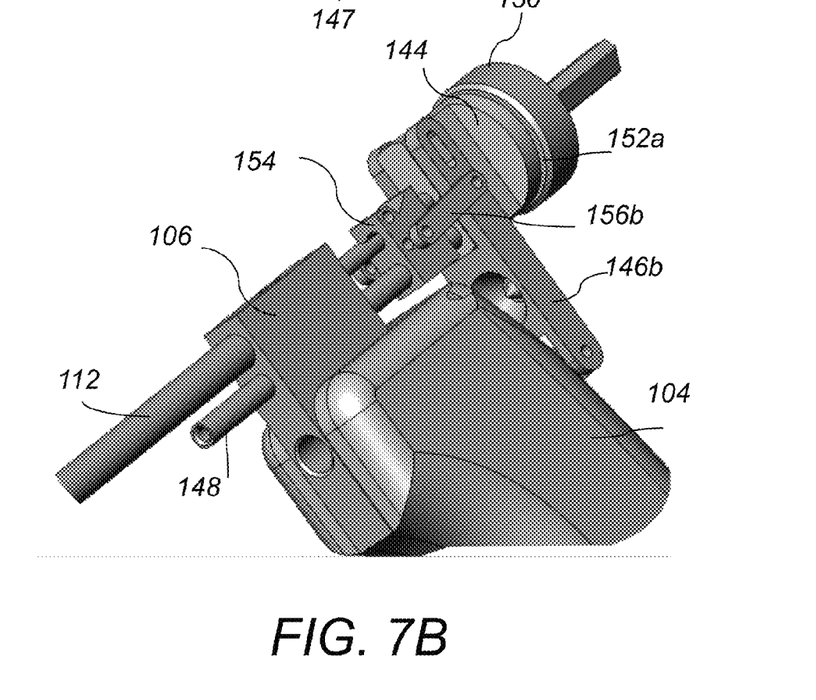
FIG. 7B depicts an enlarged left side view of the thrust assembly of the drill bit guidance device of FIG. 2A.

Referring to FIG. 7A, FIG. 7B, FIG. 8A and FIG. 8B, thrust assembly 140 includes a shank chuck 142 that connects to the drive shaft 114, a tube bushing 144, a thrust end cap 150, thrust bushings 152*a*, 152*b*, and actuator slide 154. Thrust assembly 140 is pivotally connected to handle 106 and to actuator slide 154 via linkage assembly 146. Linkage assembly 146 includes left and right vertical links 146*a*, 146*b* that link the handle 106 to the inner tube assembly 112 via a pivot connection 147. Linkage assembly 146 also includes left and right links 156*a*, 156*b* that provide a straight link between the left and right links 146*a*, 146*b* and the actuator slide 154. In the embodiment of FIG. 6A and FIG. 6B, linkage assembly 146 also includes left and right links 158*a*, 158*b* that provide a straight link between the actuator slide 154 and the thrust end cap 150.

Figure 2B:
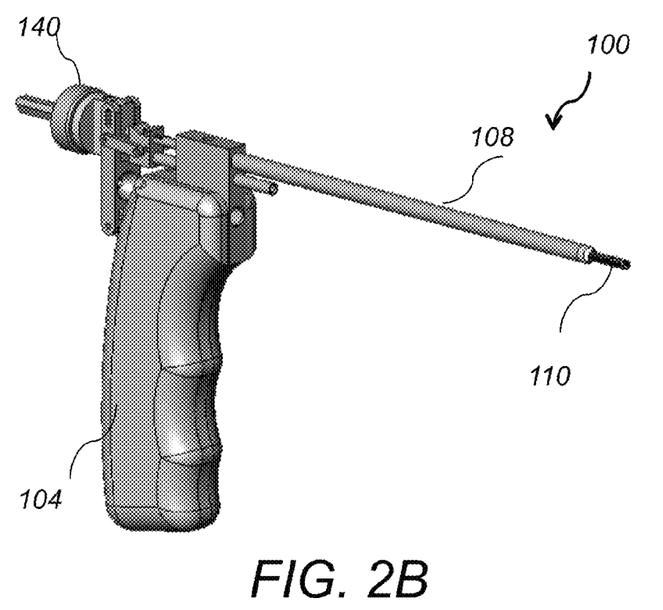
FIG. 2B is a perspective view of the drill bit guidance device of FIG. 2A with the slotted tube in the "straight" position.
Figure 2C:
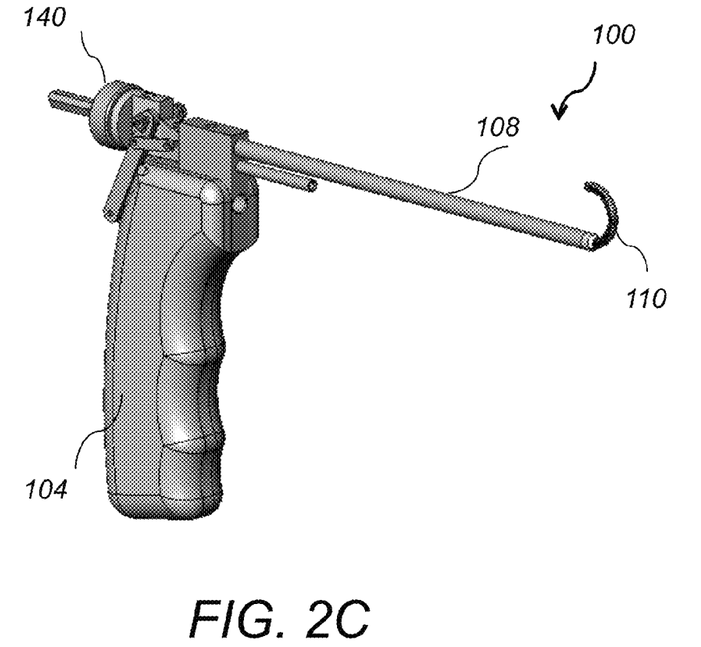
FIG. 2C is a perspective view of the drill bit guidance device of FIG. 2A with the slotted tube in the "curved" position.
Figure 5D:
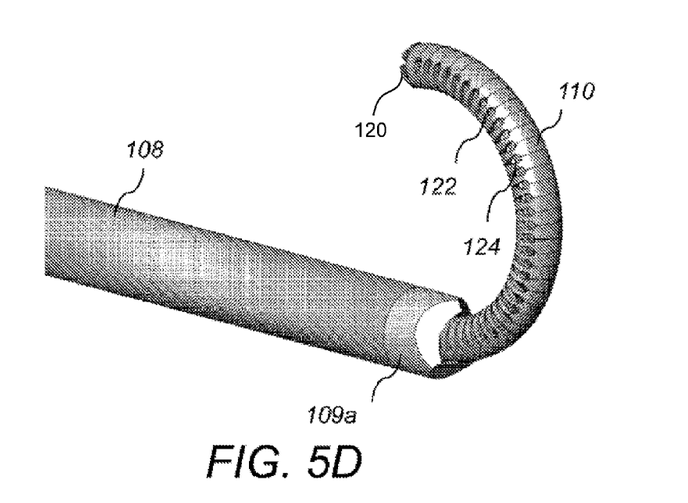
FIG. 5D depicts the distal end of the drill bit guidance device of FIG. 2A with the slotted tube in the "curved" position.

In operation, as the drill bit 120 feeds out of the outer tube 108, the slotted front end of tube 110 that is connected to the drill bit 120 follows. As each slot 122 of the slotted tube front exits the outer tube 108, it collapses inward in the slot direction. This inward collapse of the slots 122 causes the length of the slotted tube 110 to become shorter than the length of the drive shaft 114 and this results in curving of the flexible shaft 116, which in turn causes the drill bit 120 to follow a curved path as it moves forward. The ratio of the length of the drive shaft 114 to the length of the collapsed slotted tube 110 remains constant throughout the entire range of the drill bit movement causing the radius of the curved path to remain constant. Flexible actuator rod 118 is connected to the distal end of the slotted tube 110 and causes each slot 122 to collapse as it exits the outer tube 108. In this embodiment, the actuator slide 154 and the slotted tube 110 move at different rates, thereby causing the slots 122 to collapse. Drill bit 120 and drive shaft 114 move the same amount as the slotted tube 110. The length of the slotted tube 110 is different than the length of the flexible shaft 116 in the curved position. This results in the drill bit 120 moving away from the front end bushing 161. Flexible actuator rod 118, drive shaft 114 with the attached drill bit 120 and the slotted tube 110 are connected through a linkage assembly 146 at the proximal end of the device. The linkage 146 provides the proper feed ratio so that the drill bit 120 moves in a curved path with a predetermined radius. FIG. 2A depicts the drill bit guidance device 100 with the slotted tube in the start position. FIG. 2B depicts the drill bit guidance device 100 with the slotted tube in the "straight" position. FIG. 2C depicts the drill bit guidance device 100 with the slotted tube in the "curved" position. FIG. 5C depicts the distal end of the slotted tube in the "straight" position and FIG. 5D depicts the distal end of the slotted tube in the "curved" position.

FIG. 6A and FIG. 6B depict side views of another embodiment of the drill bit guidance device 100 with the slotted tube in the "straight" and "curved" positions, respectively. In this embodiment, linkage assembly 146 includes left and right vertical links 146*a*, 146*b*, left and right links 156*a*, 156*b* and left and right links 158*a*, 158*b*. Left and right vertical links 146*a*, 146*b* link the handle 106 to the inner tube assembly 112 via a pivot connection 147. Left and right links 156*a*, 156*b* provide a straight link between the left and right links 146*a*, 146*b* and the actuator slide 154. Left and right links 158*a*, 158*b* provide a straight link between the actuator slide 154 and the thrust end cap 150. In this embodiment, slotted tube 110, actuator slide 154 and drive shaft assembly feed out at different ratios. This keeps the drill bit 120 and the front end bushing 16 at the same spacing throughout the entire range of motion. In other embodiments, a gear mechanism or a cam mechanism is used instead of the linkage assembly 146 to control the ratio of the slotted tube 110 and actuator rod 118 length to the length of the drive shaft 114.

Several embodiments of the present invention have been described. Nevertheless, it will be understood that various modifications may be made without departing from the spirit and scope of the invention. Accordingly, other embodiments are within the scope of the following claims.

What is claimed is:

1. A drill system for forming a curved tunnel in a bone, the system comprising:
   a drill bit guidance device comprising:
      an elongated stationary outer tube extending along a first axis; and
      an elongated inner tube configured to slidably move within the elongated stationary outer tube along the first axis and to exit from a distal end of the elongated stationary outer tube, wherein:
         the elongated inner tube comprises a partially slotted distal end portion comprising a plurality of semi-cross-sectional slots extending perpendicular to the first axis; and
         each of the semi-cross-sectional slots is configured to collapse inward in a direction of the slot when exiting the distal end of the elongated stationary outer tube, thereby curving the partially slotted distal end portion of the elongated inner tube;
      a drive shaft disposed within the elongated inner tube; and
      a flexible actuator rod arranged parallel to the drive shaft, wherein a distal end of the flexible actuator rod is attached to the partially slotted distal end portion of the elongated inner tube.

2. The drill system of claim 1, wherein the drill bit guidance device further comprises at least one of a flexible shaft and a drill bit.

3. The drill system of claim 2, wherein the flexible shaft comprises at least one of Nitinol wire and stainless steel wire.

4. The drill system of claim 2, wherein the drill bit guidance device comprises each of the flexible shaft and the drill bit.

5. The drill system of claim 4, wherein the elongated inner tube surrounds the drive shaft, the flexible shaft, and the flexible actuator rod.

6. The drill system of claim 5, wherein:
the drill bit is attached to a distal end of the flexible shaft;
a distal end of the drive shaft is attached to a proximal end of the flexible shaft; and
the curving of the partially slotted distal end portion of the elongated inner tube is configured to curve the flexible shaft and to guide the attached drill bit along a curved path.

7. The drill system of claim 4, wherein:
the drill bit is attached to a distal end of the flexible shaft; and
a distal end of the drive shaft is attached to a proximal end of the flexible shaft.

8. The drill system of claim 4, wherein the curving of the partially slotted distal end portion of the elongated inner tube is configured to curve the flexible shaft and to guide the attached drill bit along a curved path.

9. The drill system of claim 8, wherein a radius of the curved path is configured to remain constant by maintaining constant a ratio of a length of the drive shaft to a length of the collapsed partially slotted distal end portion of the elongated inner tube.

10. The drill system of claim 1, wherein:
the drill bit guidance device further comprises a universal grip, a handle block, a thrust assembly, and a linkage assembly;
the universal grip is attached to the handle block; and
the handle block comprises a first through-opening dimensioned to receive the elongated stationary outer tube.

11. The drill system of claim 10, wherein:
the thrust assembly is pivotally linked to the handle block via the linkage assembly and comprises a shank chuck, a tube bushing, a thrust end cap, first and second thrust bushings, and an actuator slide;
the actuator slide comprises a second through-opening dimensioned to receive the elongated inner tube; and
a proximal end of the drive shaft is connected to the shank chuck.

12. The drill system of claim 11, wherein:
a proximal end of the elongated inner tube, the proximal end of the drive shaft, and a proximal end of the flexible actuator rod are linked together via the linkage assembly; and
the linkage assembly is configured to maintain constant a ratio of a length of the drive shaft to a length of the collapsed partially slotted distal end portion of the elongated inner tube.

13. The drill system of claim 12, wherein the linkage assembly comprises first and second vertical links configured to pivotally link the handle block to the elongated inner tube.

14. The drill system of claim 13, wherein the linkage assembly further comprises first and second horizontal links configured to pivotally link the actuator slide to the first and second vertical links, respectively.

15. The drill system of claim 14, wherein the linkage assembly further comprises third and fourth horizontal links configured to pivotally link the actuator slide to the thrust end cap.

16. The drill system of claim 10, wherein the thrust assembly is linked to the handle block via a gear mechanism.

17. The drill system of claim 10, wherein the thrust assembly is linked to the handle block via a cam mechanism.

18. The drill system of claim 1, wherein each of the semi-cross-sectional slots is wider at a bottom portion thereof than at a top portion thereof.

19. The drill system of claim 1, further comprising a drill driver comprising a front opening configured to receive removable attachments, wherein the drill bit guidance device is configured to be removably attached to the front opening of the drill driver.

20. A drill system for forming a curved tunnel in a bone, the system comprising:
a drill bit guidance device comprising:
an elongated stationary outer tube extending along a first axis; and
an elongated inner tube configured to slidably move within the elongated stationary outer tube along the first axis and to exit from a distal end of the elongated stationary outer tube, wherein:
the elongated inner tube comprises a partially slotted distal end portion comprising a plurality of semi-cross-sectional slots extending perpendicular to the first axis; and
each of the semi-cross-sectional slots is configured to collapse inward in a direction of the slot when exiting the distal end of the elongated stationary outer tube, thereby curving the partially slotted distal end portion of the elongated inner tube; and
a drive shaft, a flexible shaft, a drill bit, and a flexible actuator rod, wherein:
the elongated inner tube surrounds the drive shaft, the flexible shaft, and the flexible actuator rod;
the drill bit is attached to a distal end of the flexible shaft;
a distal end of the drive shaft is attached to a proximal end of the flexible shaft;
the flexible actuator rod is arranged parallel to the drive shaft;
a distal end of the flexible actuator rod is attached to the partially slotted distal end portion of the elongated inner tube; and
the curving of the partially slotted distal end portion of the elongated inner tube is configured to curve the flexible shaft and to guide the attached drill bit along a curved path.

21. A drill system for forming a curved tunnel in a bone, the system comprising:
a drill bit guidance device comprising:
an elongated stationary outer tube extending along a first axis; and
an elongated inner tube configured to slidably move within the elongated stationary outer tube along the first axis and to exit from a distal end of the elongated stationary outer tube, wherein:
the elongated inner tube comprises a partially slotted distal end portion comprising a plurality of semi-cross-sectional slots extending perpendicular to the first axis; and
each of the semi-cross-sectional slots is configured to collapse inward in a direction of the slot when exiting the distal end of the elongated stationary outer tube, thereby curving the partially slotted distal end portion of the elongated inner tube; and
a drive shaft disposed within the elongated inner tube; and a universal grip, a handle block, a thrust assembly, and a linkage assembly, wherein:

the universal grip is attached to the handle block;

the handle block comprises a first through-opening dimensioned to receive the elongated stationary outer tube; and the thrust assembly is pivotally linked to the handle block via the linkage assembly and comprises a shank chuck, a tube bushing, a thrust end cap, first and second thrust bushings, and an actuator slide, wherein:

the actuator slide comprises a second through-opening dimensioned to receive the elongated inner tube; and a proximal end of the drive shaft is connected to the shank chuck.

\* \* \* \* \*